(12) United States Patent
Diederichs

(10) Patent No.: US 7,635,830 B2
(45) Date of Patent: Dec. 22, 2009

(54) OPTICAL SYSTEM FOR FORMING AN ILLUMINATED PATTERN ON A MATERIAL IN MOTION AND WHICH ILLUMINATED PATTERN IS SYNCHRONIZED WITH A DETECTION DEVICE

(75) Inventor: Carsten Diederichs, Lemgo (DE)

(73) Assignee: Koenig & Bauer Aktiengesellschaft, Wurzburg (DE)

( * ) Notice: Subject to any disclaimer, the term of this patent is extended or adjusted under 35 U.S.C. 154(b) by 239 days.

(21) Appl. No.: 10/593,728

(22) PCT Filed: Mar. 15, 2005

(86) PCT No.: PCT/EP2005/051161

§ 371 (c)(1), (2), (4) Date: Sep. 20, 2006

(87) PCT Pub. No.: WO2005/092619

PCT Pub. Date: Oct. 6, 2005

(65) Prior Publication Data

US 2008/0164430 A1 Jul. 10, 2008

(30) Foreign Application Priority Data

Mar. 23, 2004 (DE) .................. 10 2004 014 532

(51) Int. Cl.
*G01J 1/32* (2006.01)

(52) U.S. Cl. ............... 250/205; 250/559.03; 356/237.1; 382/135

(58) Field of Classification Search ............ 250/208.1, 250/208.2, 559.08, 559.4, 206, 223 R, 223 B, 250/205, 221, 559.03; 348/295, 296, 297, 348/298, 88; 356/237.1, 239.3, 237.2, 237.4, 356/237.5; 315/291; 382/135, 321, 137–140, 382/181, 190, 191

See application file for complete search history.

(56) References Cited

U.S. PATENT DOCUMENTS

| 4,280,624 | A | * | 7/1981 | Ford | .................. 209/524 |
| 4,567,506 | A | | 1/1986 | Shinoda et al. | |
| 4,791,493 | A | | 12/1988 | Ogura et al. | |
| 4,972,093 | A | | 11/1990 | Cochran et al. | |
| 5,237,181 | A | | 8/1993 | Kerkhoff et al. | |
| 5,591,899 | A | * | 1/1997 | Griesbeck | .................. 73/41 |
| 5,717,790 | A | | 2/1998 | Kanesaka et al. | |
| 5,724,437 | A | | 3/1998 | Bucher et al. | |

(Continued)

FOREIGN PATENT DOCUMENTS

| DE | 35 27 300 A1 | 2/1986 |
| DE | 41 02 122 A1 | 7/1992 |

(Continued)

OTHER PUBLICATIONS

"Secondary Optics Design Considerations for SuperFlux LEDs," D5, Application Brief AB20-5, Lumileds, San Jose, CA.

*Primary Examiner*—Thanh X Luu
*Assistant Examiner*—Francis M Legasse, Jr.
(74) *Attorney, Agent, or Firm*—Jones, Tullar & Cooper, P.C.

(57) ABSTRACT

An optical system is usable for forming an illuminated pattern on the surface of a material which is being displaced with respect to that illuminated pattern. An illuminating device, which includes several light sources that are driven in a pulsed manner by a control unit, emits light that is used to form the illuminated pattern. A detection device detects the light emitted by the illuminating device. The control unit controls one individual light source, or a group of light sources. An operating time of the light source or sources is synchronized with an exposure time of the detection device. The operating time of the light source is shorter than the exposure time of the detection device.

16 Claims, 13 Drawing Sheets

U.S. PATENT DOCUMENTS

| | | | |
|---|---|---|---|
| 5,854,680 | A | 12/1998 | Rakitsch |
| 5,936,353 | A | 8/1999 | Triner et al. |
| 5,999,636 | A | 12/1999 | Juang |
| 6,023,532 | A | 2/2000 | Kanesaka et al. |
| 6,175,107 | B1* | 1/2001 | Juvinall ................. 250/223 B |
| 6,480,280 | B1* | 11/2002 | Hinata ....................... 356/428 |
| 7,012,382 | B2* | 3/2006 | Cheang et al. .............. 315/291 |
| 2001/0054680 | A1* | 12/2001 | Lindner .................. 250/223 B |
| 2002/0171754 | A1* | 11/2002 | Lai et al. .................... 348/371 |
| 2006/0001924 | A1 | 1/2006 | Tatarczyk |

FOREIGN PATENT DOCUMENTS

| | | |
|---|---|---|
| DE | 35 27 300 C2 | 9/1992 |
| DE | 43 14 219 A1 | 11/1994 |
| DE | 43 21 177 A1 | 1/1995 |
| DE | 195 11782 C2 | 10/1996 |
| DE | 196 17 009 C2 | 5/1999 |
| DE | 100 61 070 A1 | 6/2002 |
| DE | 202 13 431 U1 | 12/2002 |
| DE | 203 03 574 U1 | 6/2003 |
| DE | 10 2004 003 613 | 8/2005 |
| EP | 0 674 425 A1 | 9/1995 |
| EP | 0 762 174 A2 | 9/1996 |
| FR | 78 00769 | 8/1978 |
| JP | 61179664 A | 8/1986 |
| JP | 1255371 A | 10/1989 |
| JP | 01255371 A | 10/1989 |
| JP | 06098096 A | 4/1994 |
| JP | 6222014 A | 8/1994 |
| JP | 8327826 A | 12/1996 |
| JP | 2000039682 A | 2/2000 |
| JP | 2001174410 A | 6/2001 |
| JP | 2001221745 A | 8/2001 |

* cited by examiner

OPTICAL SYSTEM FOR FORMING AN ILLUMINATED PATTERN ON A MATERIAL IN MOTION AND WHICH ILLUMINATED PATTERN IS SYNCHRONIZED WITH A DETECTION DEVICE

CROSS-REFERENCE TO RELATED APPLICATIONS

This patent application is the U.S. national phase, under 35 U.S.C. 371, of PCT/EP2005/051161, filed Mar. 15, 2005; published as WO 2005/092619 A1 on Mar. 23, 2004, and claiming priority to DE 10 2004 04 532.6, filed Mar. 23, 2004, the disclosures of which are expressly incorporated herein by reference.

FIELD OF THE INVENTION

The present invention is directed to an optical system for forming an illuminated pattern. The illumination pattern is formed on a surface of a material that is moving relative to the formed pattern. An illumination arrangement, with several pulsed light sources, is operated by a control device and emits light for generating the pattern.

BACKGROUND OF THE INVENTION

Optical systems for forming an illuminated structure are used primarily in connection with the recording of images of machine-processed material in the field of industrial image processing, such as, for example, in the recording of imprinted material which is processed in connection with stocks and bonds. The optical system is used in or on a printing press, preferably in or on a rotary printing press, and in particular in or on a printing press operated in, for example, an offset printing method, a steel engraving method, a screen printing method or a hot-process embossing method. Alternatively, or in addition to such an arrangement in or on a printing press, an optical system can also be arranged in or on a machine which further processes a printed product. Image recording is performed for the purpose of providing an at least partial, and preferably a complete image representation of the moving imprinted material. This image representation can be done with or without taking a measurement of previously determined characteristics of the imprinted material, in order to evaluate this material regarding the quality of a process step previously performed in the machine. Optical systems of this general type are typically employed, for example, in an inline inspection system and therefore are typically a component of such an inline inspection system.

An image reading device is known from DE 35 27 300 C2. An illumination arrangement, with several groups of light sources, is provided. The groups of light sources emit light for use in generating an illuminated strip. A control arrangement operates the groups of light sources in a pulsed manner. Photo-sensors, which are arranged in rows, detect light which is reflected from the surface of the material. The photo-sensors constitute a line-scanning camera. An electrical current source, that is controlled by the control arrangement, is assigned to the groups of light sources. A length of time, in which the light sources are switched-on, is synchronized with a length of the line-scanning camera exposure time.

A method for checking web-shaped transparent material, and in particular, for checking a paper web, which is suitable for application in the print industry, is known from DE 41 02 122 A1. Flash bulbs, which are constructed from light-emitting diodes or from laser diodes, radiate through a paper web. Light, which is being radiated through the paper web, impinges on a CCD matrix of a camera to generate a video signal. Light leaving the illumination arrangement, in the direction of the paper web, radiates through a frosted diffusor disk.

A printing press with an inline image inspection system, for use in the inspection of a printed product produced in the printing press, is known from DE 43 21 177 A1. An image detection arrangement is provided, which delivers image data of the printed product to a computing device. The image detection arrangement consists of a measuring module, or of several measuring modules, each of which scans a defined image area of the printed product, and of at least one associated receiving device. The receiving device makes the image data available in an electric form and is preferably spatially separated from the measuring modules. The measuring modules and the at least one receiving device are connected with each other by at least one image conductor. An illumination arrangement, consisting of precision halogen lamps, is assigned to the image detection device. A blow pipe, with openings in the direction of the printed product, when charged with compressed air maintains the printed product at a defined distance from the illumination arrangement and simultaneously cools the illumination arrangement by use of the blowing air.

An illumination arrangement for an optical inspection system, for use in the inspection of surfaces, is known from DE 100 61 070 A1. Several support panels, which are preferably of the same length and are electrically connected with each other, and each of which is provided with several rows of light-emitting diodes, have been inserted in a line-shaped manner into a common rigid, profiled mounting device. The mounting device can be cut in length to correspond to an object surface which is to be scanned by the use of constant light radiation. A thermal connection between the support panels and the profiled mounting device, for cooling the light-emitting diodes and their electronic control device, is provided by a mechanical connection.

A device for the quality control of printed matter is known from DE 202 13 431 U1. This device constitutes an inline image inspection system which is arranged in a printing press. An illumination arrangement, configured as a fluorescent tube, and an image recording device, configured as a line-scanning camera, are employed.

An inline image inspection system for a printing press, and in particular for a sheet-fed offset printing press, is known from DE 203 03 574 U1. An illumination arrangement that is configured as a fluorescent tube, is arranged underneath a foot pedal and close to a counter-pressure cylinder which is conveying an imprinted material. An image recording device, which is provided as a line-scanning camera, is arranged at a comparatively greater distance from the counter-pressure cylinder in association with the last printing group of the printing press.

A device for a line-shaped illumination of sheet material, such as banknotes and securities, is known from EP 0 762 174 A2. A cylindrical mirror with two mirror segments is provided. The mirror segments form an elliptical base surface having two focal lines. The width of the mirror segments has been selected to be larger than or equal to the width of the sheet material. The sheet material, which is transported in the transport direction perpendicularly to the first focal line, is arranged in this first focal line. A cold light source, such as, for example a row of light-emitting diodes (LEDs), is arranged in the second focal line. A detector, such as, for example a CCD array, or photod time in accordance with the upper, first iodes, which can be arranged individually or in groups, detects the light reflected by the sheet material and converts it into signals for processing in a processing installation.

An inspection system is known from U.S. Pat. No. 4,972,093. A moving test object is subjected to a strobe of light lasting between 20 ms and 200 ms from a light-emitting diode arrangement which is controlled in a pulse-like manner. An area-scanning camera takes a picture of the entire test object.

An optical system for forming an illuminated pattern on a surface of a material which is moved relative to the pattern is known from U.S. Pat. No. 5,936,353. An illumination arrangement with several light sources, which are switched in series, emits light for forming the pattern. A detection device, with at least one detector, detects light reflected from the surface of the material. The light sources are arranged on a panel which is arranged on a support. That support has at least one conduit in its interior. A liquid or gaseous cooling medium, for use in cooling the light sources, flows through the conduit.

A device for use in the control of light-emitting diodes with a constant current source, which form a line-shaped illumination arrangement, is known from JP 1-255 371 A. A driving circuit of the light-emitting diodes is connected with a line-scanning camera via a scanning control circuit and a multiplexer. The light-emitting diodes of the illumination arrangement, which are in operative connection with each other, and photo-sensors of the line-scanning camera are synchronized with each other.

FIELD OF THE INVENTION

The object of the present invention is directed to on providing an optical system for use in forming an illuminated pattern. A picture is taken with the same amount of light over a wide range of the speed of the moving material.

In accordance with the present invention, this object is attained by the provision of an optical system for use in generating an illuminated pattern on a surface of a material which is moving relative to the pattern. An illumination arrangement, which has several light sources that are operated in a pulsed manner by a control device, emits the light which generates the pattern. A detection device detects the light emitted by the light sources. A switched-on time of the light source is controlled by the control device and is synchronized with a length of an exposure time of the detection device. The length of the switched-on time of the light source is arranged within the exposure time of the detection device.

The advantages to be gained by the present invention consist, in particular, in that the surface of the moving material is always illuminated with the same amount of light, regardless of the speed of the moving material. Accordingly, a constant brightness results for image recording and unusable image recordings are avoided. Additionally, the length of time that the light source is switched on always constitutes a partial amount of the length of the exposure time of the line-scanning camera. A fixed correlation between the length of time that the light source is switched on, and the length of the exposure time of the line-scanning camera is always assured for the timing. A digital line-scanning camera typically has an electronic shutter which, at the end of a selected exposure time of the line-scanning camera, puts out a read-out pulse for use in reading out the electrical charge which was collected by the detectors as a result of the light reflected from the surface of the moving material. Overflowing of the detectors of the line-scanning cameras, which are sensitive to electrical charges, is avoided by the use of the correlation, in accordance with the present invention, between the time the light source is switched on and the exposure time of the line-scanning camera. In an advantageous manner, a barrier results over a wide range of the speed of the moving material and therefore provides an unequivocal separation between sequential detectors, which are successively arranged in the movement direction of the line-scanning camera.

A further advantage of the optical system in accordance with the present invention lies in that the material, on whose surface the pattern is to be created, need not be arranged in a focal point, which is located in a direct or in a redirected beam path of the light being emitted by the light source, in order to make the pattern appear with a sufficiently strong illumination. An arrangement of the pattern, relative to the optical system, which is independent of the focal point, is advantageous. In that case, it is possible to do without an exact dimensional accuracy with respect to the distance between the pattern and the illumination arrangement. The distance of the proposed optical system is therefore tolerant with respect to the illuminated material. Moreover, a sufficient distance is provided between components of the optical system, whose functioning could be impaired by soiling, such as, for example, by dust or by rubbed-off particles, and the material. In particular, in regard to a transport device which moves the material, this sufficient distance, under the existing operating conditions in a printing press, keeps the optical system and the material out of direct contact. This sufficient distance also preferably arranges the optical system outside the range of particles of dirt which may be stirred up by the moving material.

An illuminated strip, which is illuminated by the illumination arrangement and which is of a width that extends orthogonally on the surface of the material, with respect to its length, i.e. a two-dimensional flat pattern, has an advantage over a line-shaped, or an only one-dimensional illuminated pattern, which is focused on a focal point. The illuminated pattern dependably appears to a detection device as a virtual, line-shaped illumination arrangement for detecting the light reflected by the surface of the material. That material is arranged at a reflective angle with respect to a surface of the material, which is reflective at least in part, even if the surface of the material is configured to be in a relief shape. It is assured, based on the width of the illuminated strip, that a cross-sectional surface of a detection angle of the detection device, which exists on the surface of the material and within which the detection device is capable of detecting reflected light, will detect at least a portion of a cross-sectional surface of the light beam emitted by the illumination arrangement which extends over the width of the illuminated strip. There is the danger, in connection with a device which illuminates the material only in a line-like manner, that the focused light beams may be reflected by a relief-like surface of the material outside of the detection angle of the detection device, so that, as a result, the focused light beam cannot be detected. In contrast thereto, the optical system in accordance with the present invention is also well suited for taking pictures of material with a diffusely reflecting surface. A shading effect very rarely occurs, even with a material having a relief-like surface.

The illumination arrangement of the optical system of the present invention is preferably constructed by the use of modules, such as, for example in independent functional units. This construction has the advantage that the length of a line of the line-shaped illumination arrangement can be adapted, without an expensive special production, by the use of a simple alignment of prefabricated, preferably functionally identical modules, in the required amounts, to the width of the material to be illuminated, or at least to the width of the illuminated strip. It is possible, in the same way, to activate the light sources, in a selective positive manner, only in those modules which are required for illuminating the width of the material to be illuminated, or for illuminating at least the length of the illuminated strip. Such an activation has advantages with respect to the efficiency of the construction and the operation of the optical system.

The employment of a plurality of light sources for each module has the advantage that differences in the light emitted by the light sources, which differences are unavoidable in actual use, and which differences may exist in, for example, its wavelength, are compensated for by mixing the light beams of adjoining light sources. In this way, the optical properties of the light emitted, as a whole, by the illumination arrangement are homogenized. Preferably, if several groups of light sources are arranged in each module, and wherein the light sources that are assigned to the groups differ in their optical properties, such as, for example in the color of the light emitted by the light sources of each group, the individual groups of light sources can be selected in accordance with their application, such as, for example, by color, and can be controlled.

The optical system in accordance with the present invention has the advantage that it charges an illuminated strip which possibly has a considerable length, of, for example, more than a meter, with a homogeneous, sufficiently large illumination strength, by the use of an even light distribution in accordance with the requirements. The optical system can be adapted, in a simple way, to the respective requirements in connection with a printing press because of its modular construction, which is not very susceptible to interference. The material to be illuminated need not be arranged in a focal point of the illumination arrangement. Accordingly, the requirement for an exact alignment of the vertical distance of the light sources with respect to the surface of the material, as well as the monitoring of this distance during the running employment of the optical system, can also be omitted. This considerably simplifies the manipulation of the optical system at the site in an industrial installation.

BRIEF DESCRIPTION OF THE DRAWINGS

Preferred embodiments of the present invention are represented in the drawings and will be explained in greater detail in what follows.

Shown are in.

DESCRIPTION OF THE PREFERRED EMBODIMENT

Figure 1:
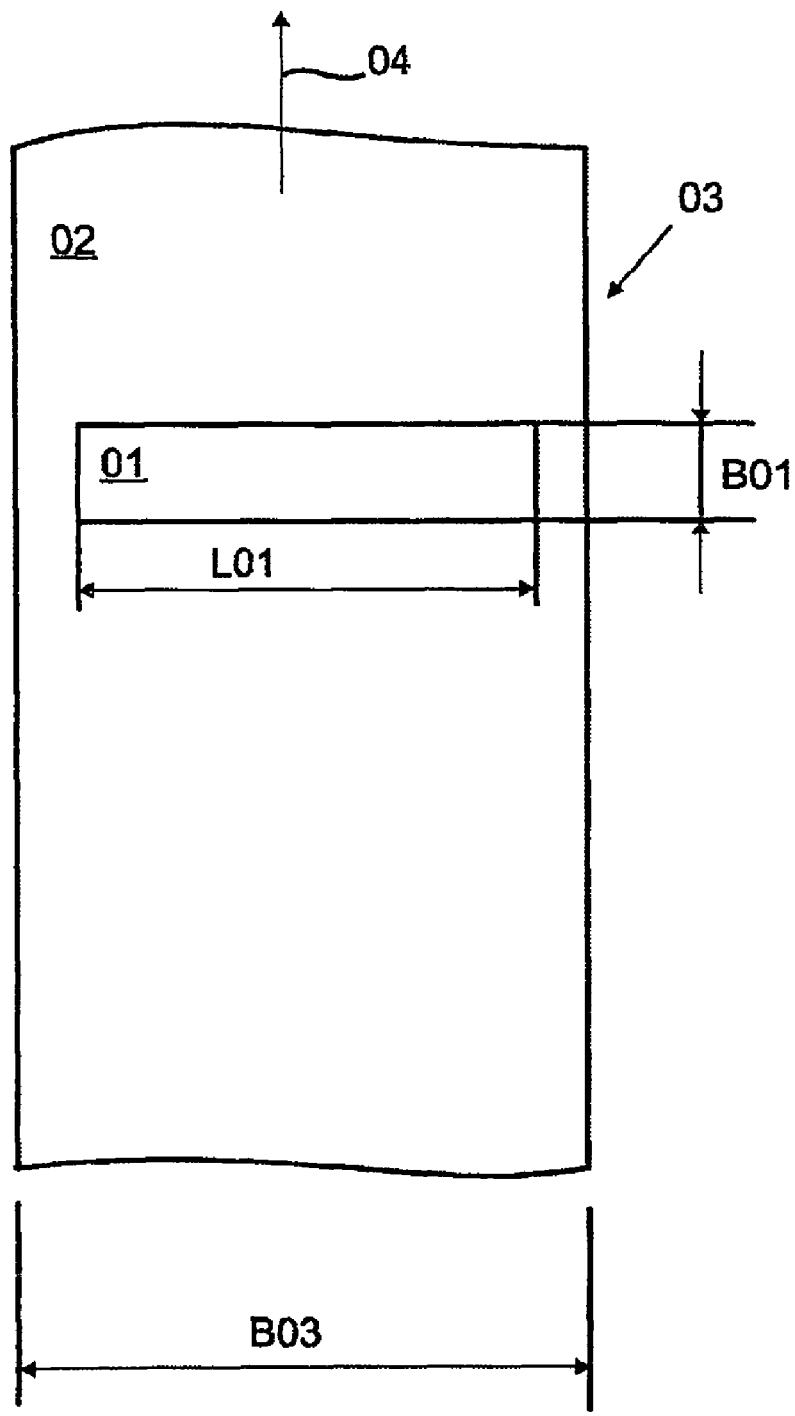
FIG. 1, a schematic top plan view a surface of a moving material with an illuminated strip, in FIG. 2, a schematic representation of the optical system in accordance with the present invention, in FIG. 3, an individual light source of the illumination arrangement, in FIG. 4, a line-like arrangement of light sources on a common board, in FIG. 5, a light beam concentration by the use of a first mirror, in FIG. 6, a light beam concentration by the use of a first mirror, along the length of the illuminated strip, in FIG. 7, a redirection of the light beam out of a central area of the light source by the use of a second mirror, in FIG. 8, a redirection of the light beam out of a central area of the light source by the use of a second mirror, and wherein the beam is more tightly focused along the length of the illuminated strip than along its width, in FIG. 9, a schematic depiction of a focusing of the beam from a central area of the light source by the use of a convex lens, in FIG. 10, a schematic depiction of a focusing of the beam from a central area of the light source by the use of a convex lens, wherein the beam is more tightly focused along the length of the illuminated strip than along its width, in FIG. 11, a schematic depiction of an at least partial superimposition of the beams from two adjoining light sources with a scattering body placed in front, in FIG. 12, a side elevation view of the optical system, in FIG. 13, a schematic depiction of a board equipped with light sources on a support through which a cooling medium flows, in FIG. 14, a schematic depiction of a support through which cooling medium flows in two opposite directions, in FIG. 15, a schematic depiction of a support with a cooling device with two Peltier elements, in FIG. 16, a representation of the chronological behavior of the line-scanning camera and of that of the light sources, and in FIG. 17, a perspective plan view of a reflector module in accordance with the present invention.

A material 03 with a surface 02, as represented in FIG. 1, is moved in a movement direction 04, indicated by an arrow, in a printing press, and in particular in a printing press which operating by the use of an offset printing process. The movement takes place by use of a transport device, which is not specifically represented, and which arranged in or on the printing press. The movement of the material 03, in the course of the operation of the optical system, which operation will be described in greater detail in what follows, preferably occurs in only one movement direction 04, and this movement directed 04 is preferably linearly. The speed of the moving material can be constant, or can also be variable.

Preferably, the material 03 is embodied with a level surface and is flat, and is provided, for example, as a sheet 03 or as a web 03 of material. In particular, the material 03 is embodied as an imprinted material 03, consisting of for example, paper and, particularly, in the form of securities 03 or as a banknote 03. The surface 02 of the material 03 can have a relief shape or can have other structure irregularities protruding from the surface 02, or from a structure which is embossed into the surface 02 in the form of a depression. The height or the depth of the relief or of the structure is very little in comparison with a width B03 of the material 03. At least a portion of the surface 02 of the material 03 is embodied to be reflective, such as, for example, by the application of a reflective material, for example a lacquer, or a foil, through the introduction of a window thread or another, preferably metallic substance into the material 03.

Figure 2:
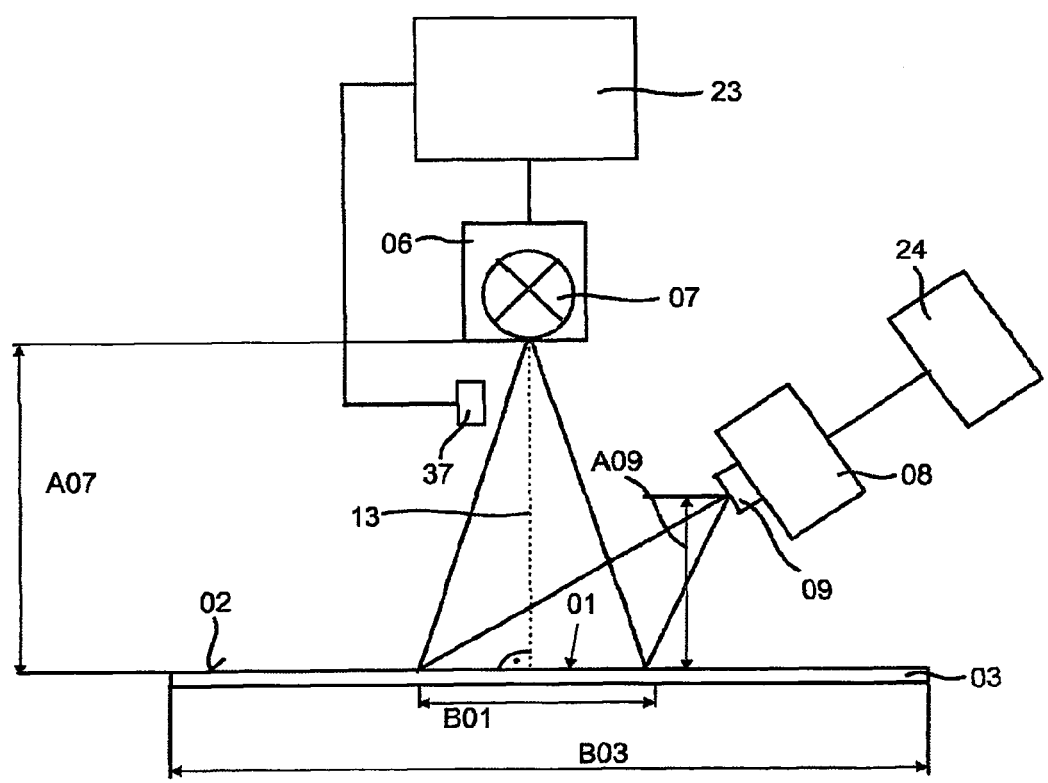

An illumination arrangement 06, which is only schematically represented in FIG. 2, forms an illuminated pattern 01, preferably in the form of an illuminated strip 01 of a length L01 and a width B01, as seen in FIG. 1, wherein the width B01 of the illuminated strip 01 extends on the surface 02 of the material 03 orthogonally in relation to the length L01 of the illuminated strip. Preferably, the width B01 of the illuminated strip 01 is oriented in, or extends in, the movement direction 04 of the material 03, while the length L01 of the illuminated strip 01 is preferably oriented parallel with the width B03 of the material 03. Length L01 can extend over portions of the width B03 of the material 03 or over its entire width B03. For example, the width B01 of the illuminated strip 01 is at least 3 mm, preferably is at least 8 mm. Therefore, the movement direction 04 of the material 03 is directed at least substantially parallel with respect to the width B01 of the illuminated strip 01. The movement direction 04 of the material 03 lies within the plane defined by the length L01 and the width B01 of the illuminating strip 01. Preferably, the material 03 does not bulge, at least in the area of the illuminated strip 01.

Referring again to FIG. 2, the illumination arrangement 06 has a plurality of light sources 07 which are arranged side-by-side in a line-shaped or linear manner, so that the entire illumination arrangement 06 is embodied to be line-shaped or linear. The light sources 07 of the illumination arrangement 06, arranged in a line-shaped or linear manner, are preferably arranged parallel with respect to the length L01 of the illuminated strip 01. The light sources 07 have a respective distance A07 from the surface 02 of the material 03. That distance A07 preferably lies between 30 mm and 200 mm, and in particular lies between 70 mm and 140 mm. Preferably, the distance A07 respectively extends perpendicularly with respect to the surface 02 of the material 03. All of the light sources 07 of the illumination arrangement 06 are preferably identically configured, such as, for example, as bright, high-intensity light-emitting diodes 07, or as laser diodes 07. It is also possible to provide separate groups of several light sources 07, each being respectively arranged in a line-shape or linear array, side-by-side, in the illumination arrangement 06. The individual groups of light sources 07 differ in their optical properties, such as, for example in the wavelength, of the light emitted by each of them. For example, one group of light sources 07 can emit white light, while another group of light sources 07 can emit monochrome light. A control device 23, which is preferably connected with the illumination arrangement 06, selects the groups of light sources 07 in accordance with the color of the light of the light sources 07 as a function of their application, such as, for example, as a function of the nature of the surface 02 of the material 03, and controls them individually. In this way, the control device 23 can also control one group of the several groups of light sources 07 independently of at least one other group of light sources 07 with respect to their brightness and/or length of illumination. The illuminated strip 01 is arranged outside of the focal point located in the direct or redirected beam path of the light emitted by the light sources 07.

Figure 12:
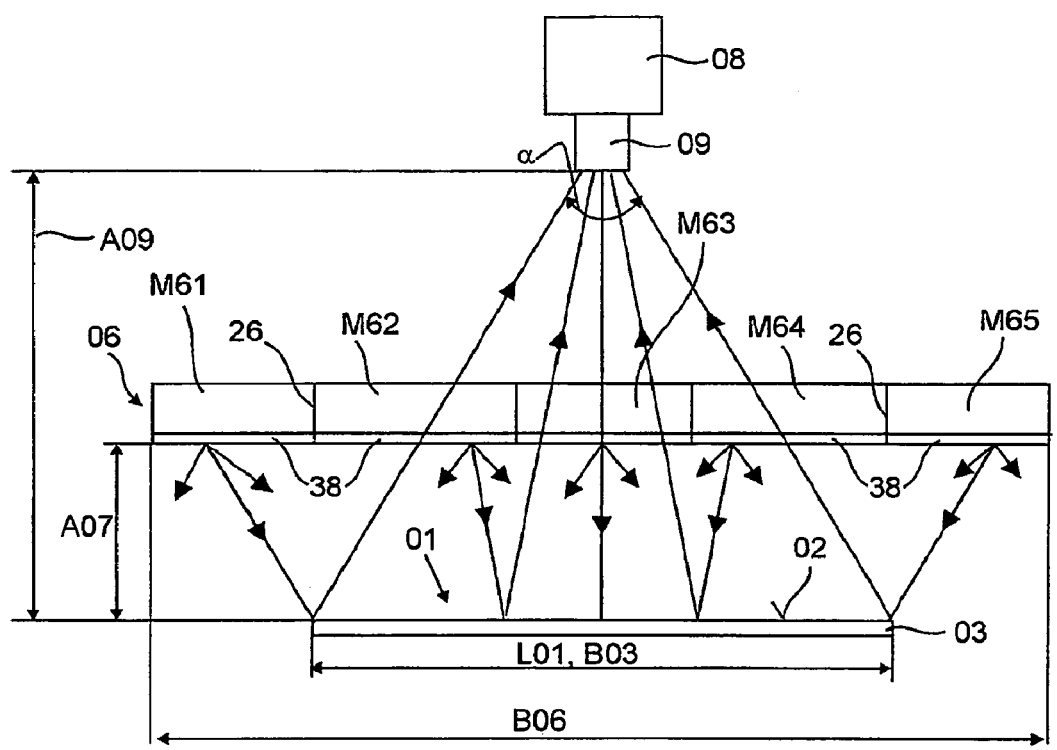

The illumination arrangement 06 can consist of, for example, several modules M61 to M65, as seen in FIG. 12, which modules M61 to M65 are aligned side-by-side in a line, with each module M61 to M65 having several light sources 07 arranged in a line next to each other. A partition 26 is arranged between two each adjoining modules M61 to M65 and is preferably arranged obliquely with respect to the length L01 of the illuminated strip 01. The individual modules M61 to M65 of the illumination arrangement 06 can each be configured to perform identical functions, for example. In this way, it is possible, for example, to activate a line length of the illumination arrangement 06, which is comprised of the several side-by-side arranged modules M61 to M65, which activated line length corresponds to the width B03 of the material 03 to be illuminated, by switching on the light sources 07, which are arranged in a line, of the modules M61 to M65 involved. Alternatively, is possible to activate a line length which corresponds to the length L01 of the illuminated strip 01 that is composed of several side-by-side arranged modules M61 to M65 by switching on the light sources 07, which are arranged in a line, of the modules M61 to M65 involved. It is also possible to activate the light sources 07 of individually selected modules M61 to M65 independently of the light sources 07 of other ones of the various modules M61 to M65.

Figure 3:
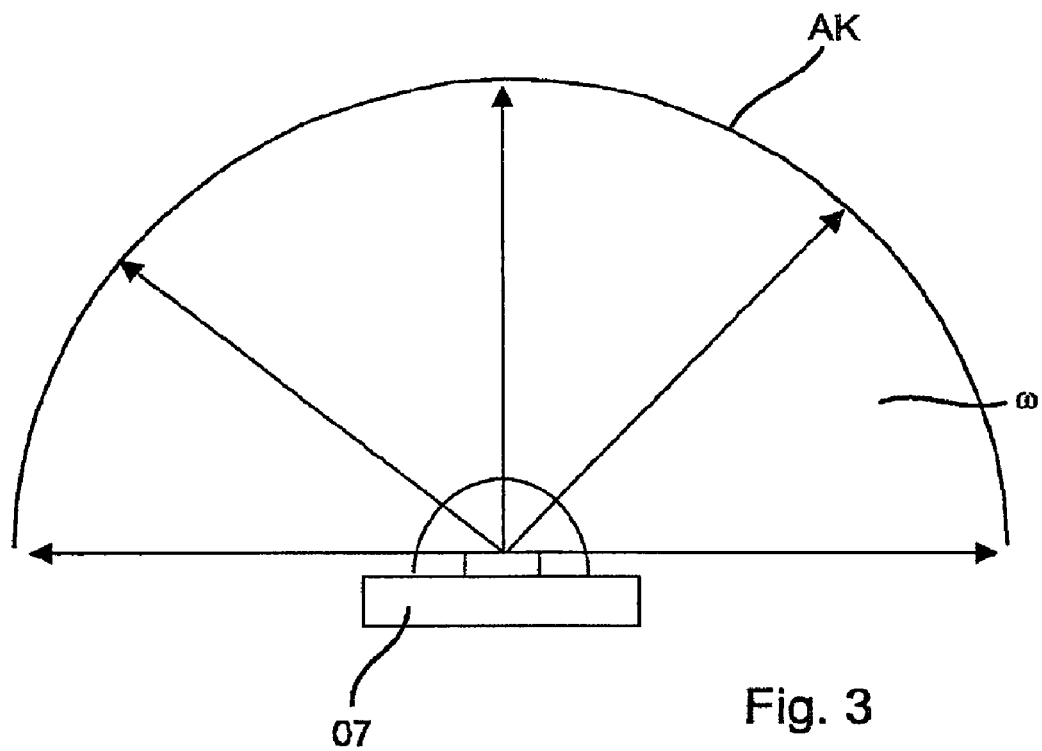

FIG. 3 shows, in a representation which is only two-dimensional, an individual light source 07 of the illumination arrangement 06. The individual light source 07 emits its light at a solid angle ω, wherein the solid angle ω covers an area AK which is cut out of a sphere, in other words an area of a surface AK of the sphere, up to the size of a hemisphere.

Figure 4:
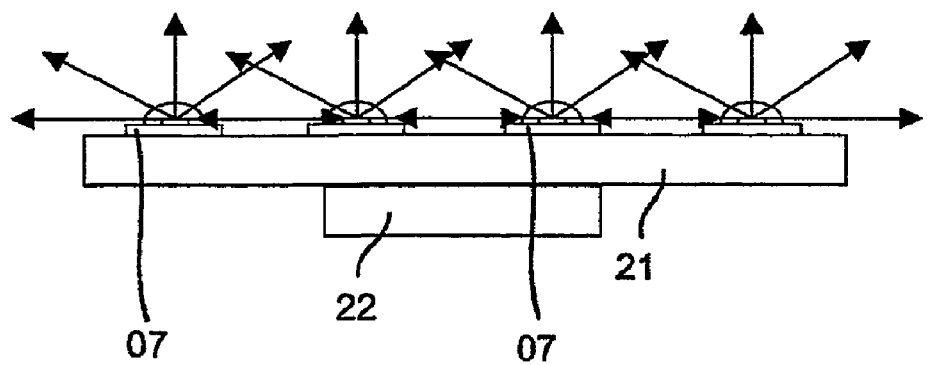

FIG. 4 depicts several, such as, for example, four, of the individual light sources 07 of the type represented in FIG. 3, which several light sources 07 are arranged next to each other in a line on a common board 21. An electrical current source 22, which is assigned to the respective light sources 07, is preferably also arranged on the same board 21. The electrical current source 22 is preferably configured as a constant electrical current source 22, and in particular as a controllable constant electrical current source 22.

An optical system is preferably a component of an inspection system that is arranged on, or in a printing press or a machine which further processes a printed product and is used for assessing the quality of a printed product that is produced by the printing press. Such an optical system includes, besides the illumination arrangement 06, such as can be taken from FIG. 2, also at least one detection device 08 with at least one detector 09, which at least one detector 09 is arranged at a distance A09 from the surface of the material 03. The detector 09 detects light reflected by the surface 02 of the material 03. The detection device 08 is configured, for example, as a camera 08, preferably as a line-scanning camera 08, and in particular as a line-scanning color camera 08. The detection device 08 also preferably has a plurality of the detectors 09 arranged side-by-side in a line next to each other. The detectors 09 which are arranged in a line, preferably are arranged parallel with respect to the length L01 of the illuminated strip 01 and/or parallel with respect to the width B03 of the material 03. A distance between lines of detectors 09, arranged in lines, preferably extends in the same direction as the movement direction 04 of the material 03. In other words, lines of the detector 09, which are arranged following each other in the movement direction 04 of the material 03, are preferably arranged orthogonally with respect to the movement direction 04 of the material 03. A detector 09 of the detection device 08 can be embodied for example as a CCD array 09 or as a group of photodiodes 09. The detector 09 of the detection device 08 converts detected reflected light into an electrical signal and supplies the electrical signal to an image processing device 24, for evaluation which image processing device 24 is connected with the detection device 08.

Figure 5:
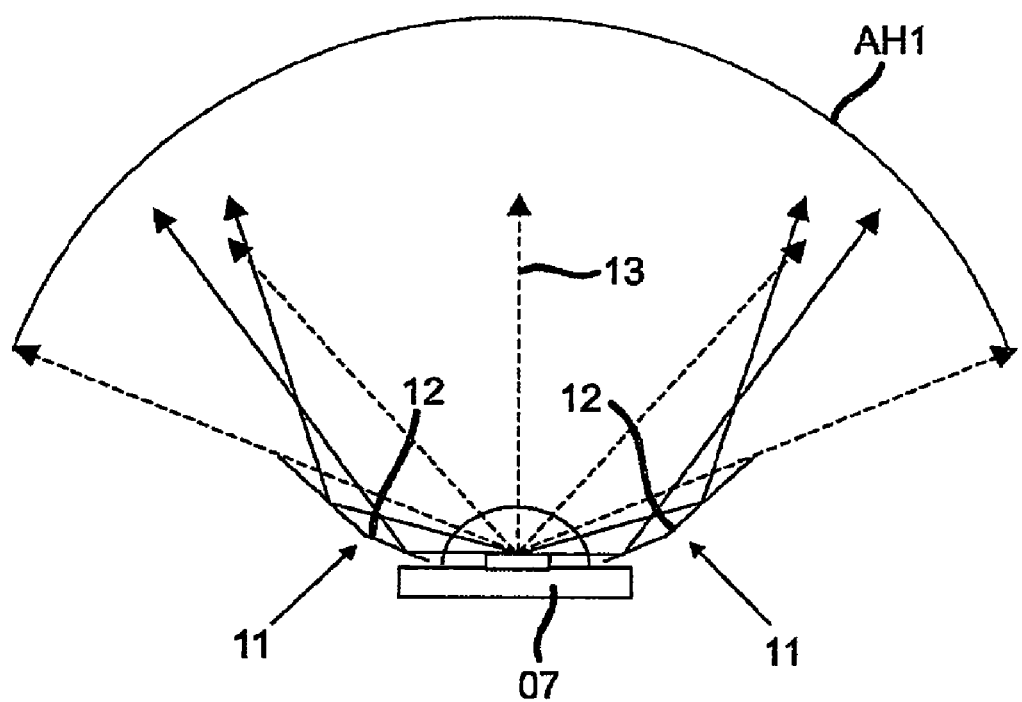
Figure 6:
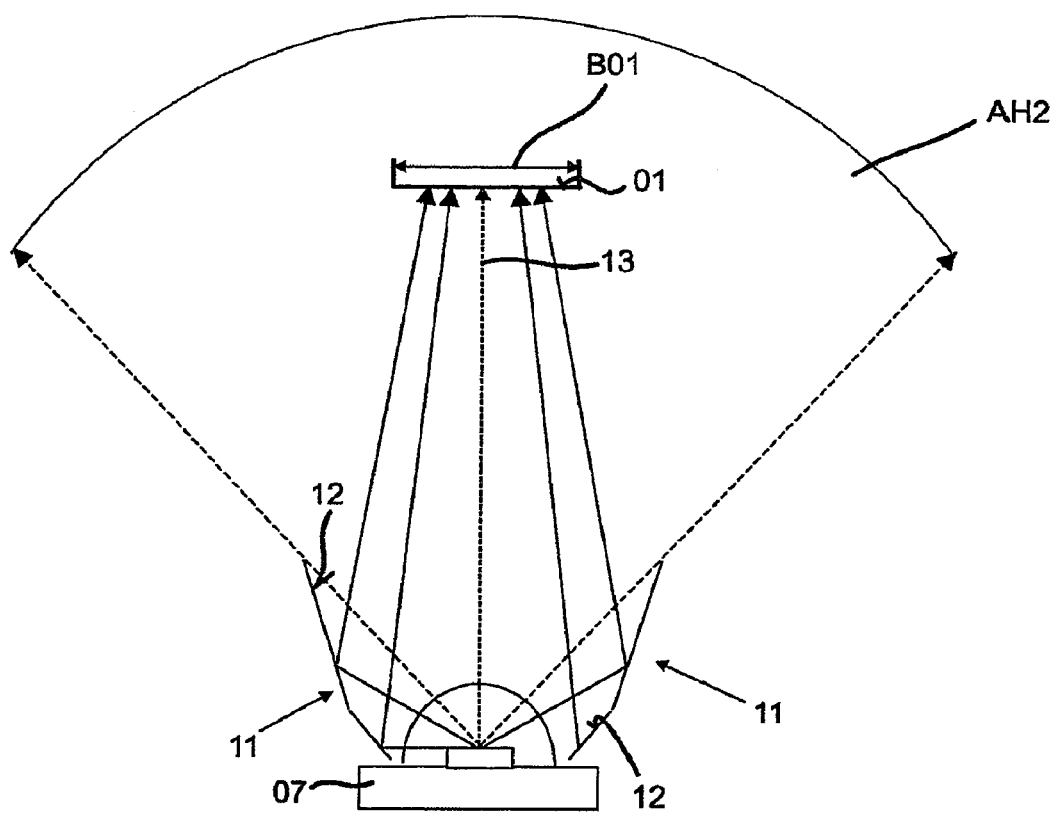

FIG. 5 shows that in the optical system in accordance with the present invention, at least one first mirror 11, with an effective surface 12 which is oriented along the length L01 and/or the width B01 of the illuminated strip 01, is assigned to the light sources 07. The effective surface 12 of the first mirror 11 restricts the light emitted in the solid angle ω, by at least one of the light sources 07 of the illuminating arrangement 06, to a first envelope surface AH1 which is smaller than the spherical surface AK which is part of the solid angle ω. The effective surface 12 of the first mirror 11 can be configured to be flat or concave. In this depicted embodiment, the at least one effective surface 12 of the first mirror 11 oriented along the length L01 of the illuminated strip 01 can restrict the light from at least one of the light sources 07 of the illumination arrangement 06 directed into the solid angle ω more closely to a second, smaller envelope surface AH2 than the at least one effective surface 12 of this first mirror 11, which is oriented along the width B01 of the illuminated strip 01, such as is shown in FIG. 6 in comparison with the beams in accordance with FIG. 5. Preferably at least one light source 07 of the illumination arrangement 06 has a first mirror 11 with at least two effective surfaces 12, which are symmetrical with respect to the central beam 13 which is emitted by the light source 07.

Figure 7:
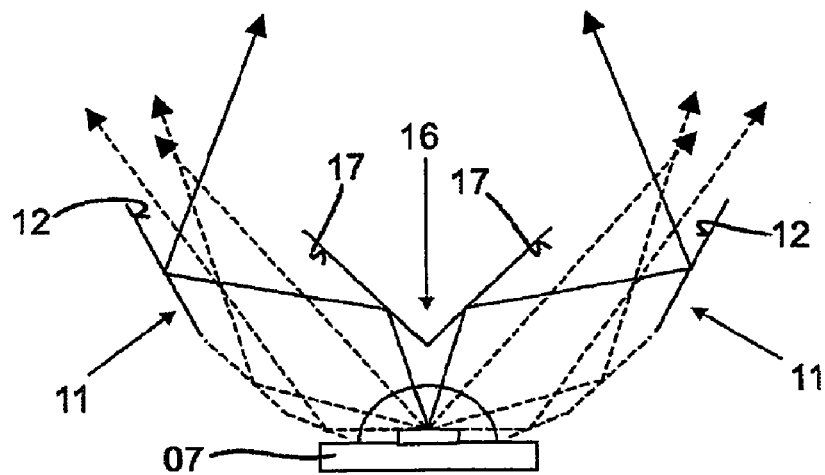
Figure 8:
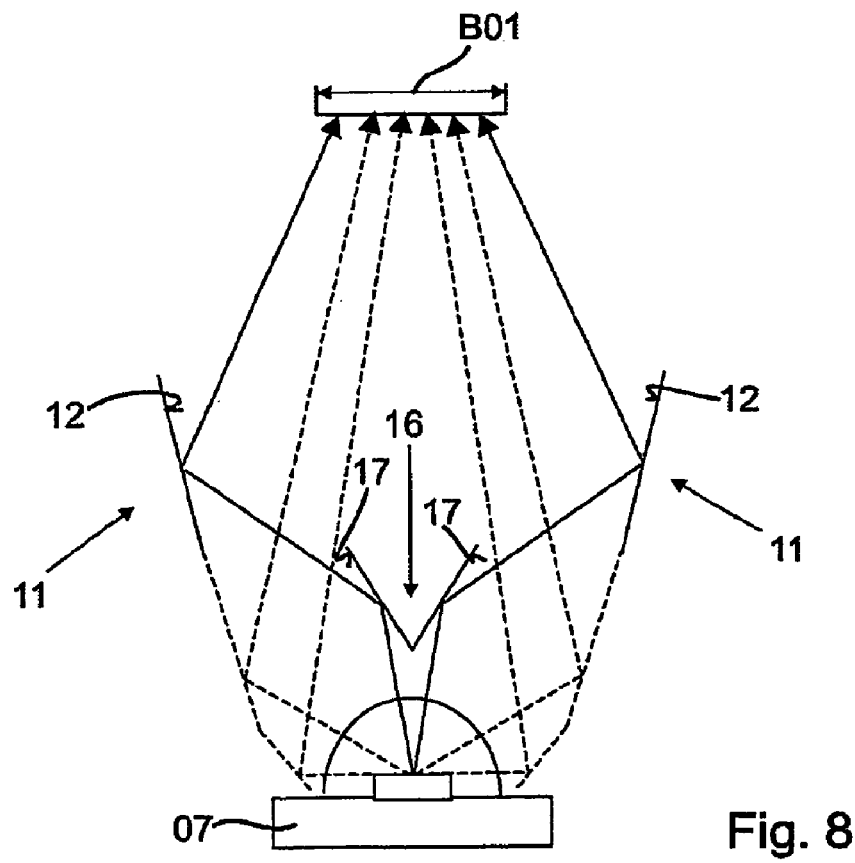

A second mirror 16 can be provided, as depicted in FIGS. 7 and 8 for use in redirecting the radiation emitted by at least one of the light sources 07 of the illumination arrangement 06 in a central area 14 surrounding the central beam 13. At least one effective surface 17 of the second mirror 16 is arranged in the central area 14 surrounding the beam path of the central beam 13, within the solid angle ω of the light emitted by the light source 07. The effective surface 17 of the second mirror 16 redirects the light emitted by at least one of the light sources 07 of the illumination arrangement 06 against at least one effective surface 12 of the first mirror 11, which at least one effective surface 12 is directed along the length L01 and/or the width B01 of the illuminated strip 01. In this case, the light which is emitted by the light source 07 can preferably be more tightly focused along the length L01 of the illuminated strip 01 than along its width B01. The effective surface 17 of the second mirror 16 can also be embodied to be flat or concave. The light beams to be assigned to the central area 14, and which are emitted by the respective light sources 07, are respectively indicated in FIGS. 7 to 10 by solid arrow lines. The light beams which are peripherally emitted in their respective solid angles ω by the light sources 07 are indicated by dashed arrow lines.

Figure 9:
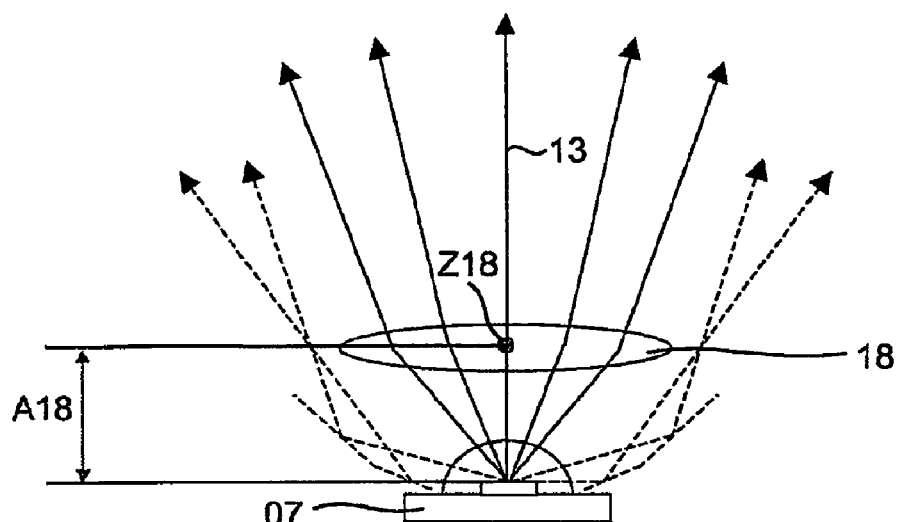
Figure 10:
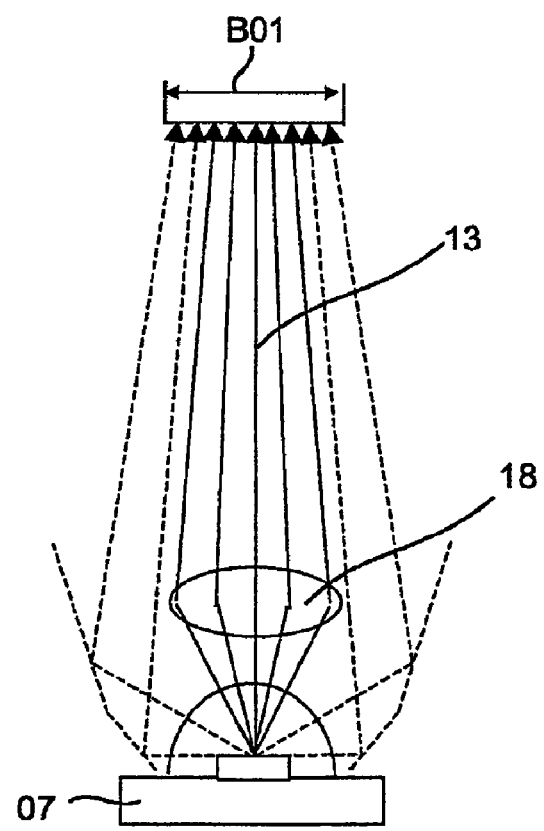

As depicted in FIGS. 9 and 10, it is alternatively also possible, in order to accomplish the redirection of the light beams which are emitted by at least one of the light sources 07 of the illumination arrangement 06 in a central area 14 surrounding the central beam 13, to arrange at least one lens 18, and in particular a biconcave lens 18, in the central area 14 surrounding the central beam 13 and within the solid angle ω of the light which is emitted by at least one of the light sources 07 of the illumination arrangement 06. A distance A18 exists between the light source 07 and a center Z18 of the lens 18. The distance A18 is advantageously less than half the distance A07 between the light source 07 and the surface 02 of the material 03. In this case, the lens 18 can be embodied to be not rotationally symmetrical. This can be done in order to preferably focus the light emitted by the light source 07 more tightly along the length L01 of the illuminated strip 01 than along its width B01.

Figure 11:
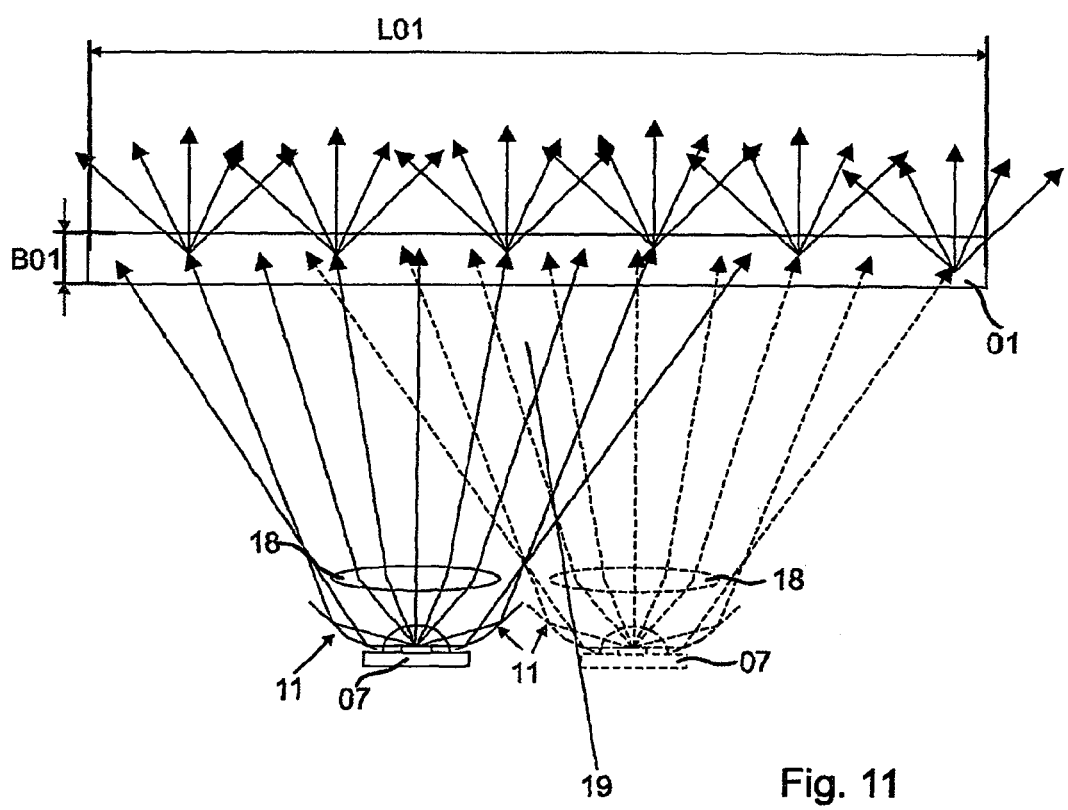

FIG. 11 shows that the light sources 07 of the illumination arrangement 06 are preferably arranged in such a way that the respective solid angles ω, or at least the envelope surfaces AH1, AH2 of the light which is emitted by at least two adjoining light sources 07 of the illumination arrangement 06, are overlaid on each other in at least a partial area 19 which illuminates the illuminated strip 01. This overlay is, in particular, also provided if the respective two adjoining light sources 07 are arranged in two adjoining modules M61 to M65. It can also be seen in FIG. 11 that a respective first mirror 11, with at least one effective surface 12, and preferably with two such effective surfaces 12, which are symmetrical in respect to each other, can be provided at each individual light source 07 of the illumination arrangement 06, at least along the width B01 of the illuminated strip 01.

Figure 17:
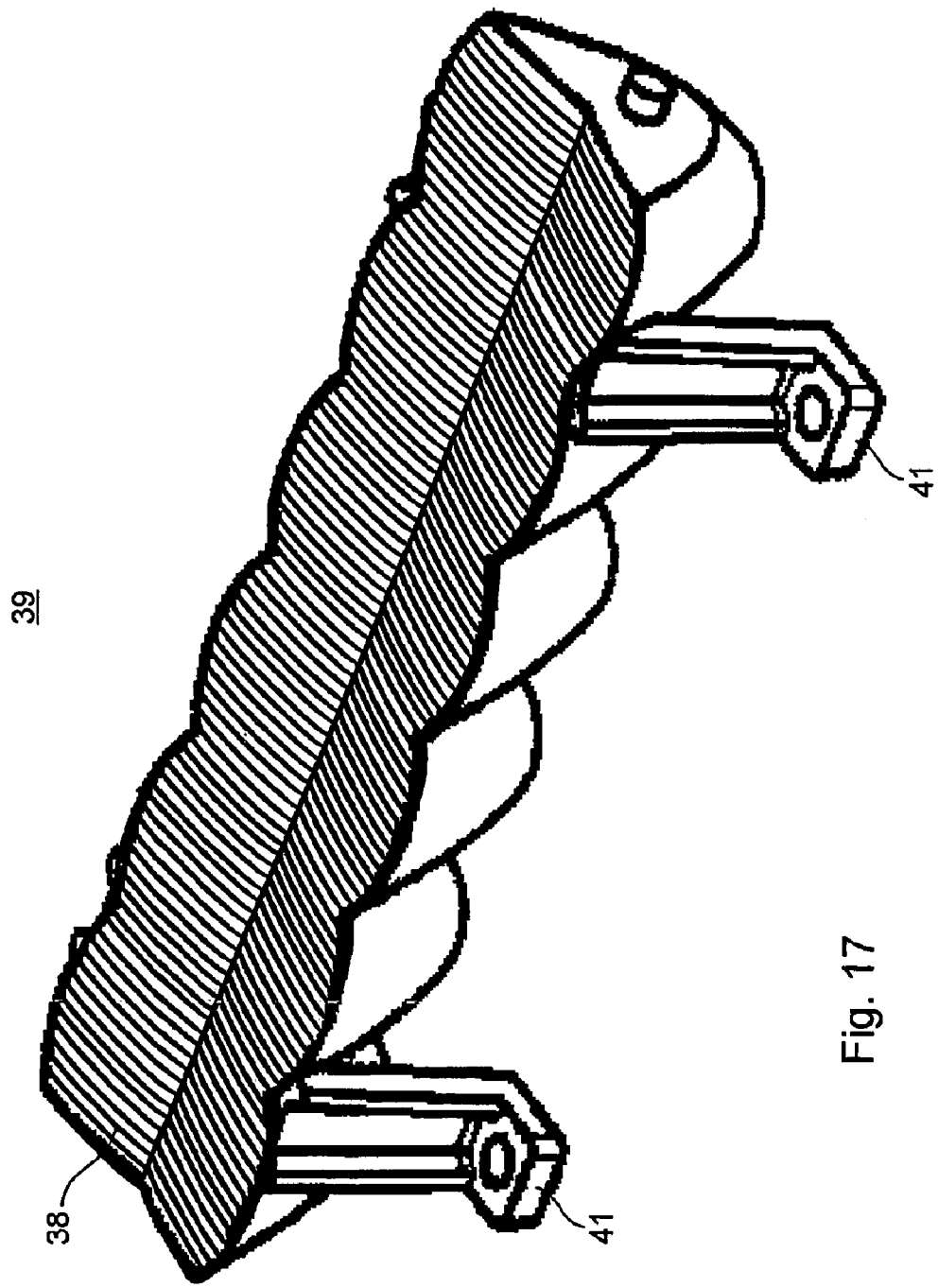

The illumination arrangement 06 can have a scattering body 38, or in other words, a light-scattering body, 38, such as for example, a lenticula or a prism foil, which may be located, as seen in FIG. 12 at a side of the illumination arrangement 06 facing the surface 02 of the material 03, i.e. at a light outlet side of the arrangement 06. The scattering body 38 distributes the light which is radiated by the light sources 07 onto the surface 02 of the material 03 preferably exclusively, or at least quite preponderantly, along the length L01 of the illuminated strip 01. In a preferred embodiment of the present invention, the scattering body 38 and at least one of the mirrors 11, 16 of the illumination arrangement 06 are embodied as a single component, called a reflector module 39 as seen in FIG. 17. A group of, for example five or ten, light sources 07 are preferably arranged in a line next to each other and respectively radiate their light into a reflector module 39 that is arranged along this row of light sources 07. For this purpose, the light sources 07 are arranged on the side of the reflector module 39 which is located diametrically opposite the light outlet side or may even be recessed in that area in a reflector module 39. The reflector module 39 is a component which has been produced, for example, from a preferably transparent material by injection-molding techniques. Therefore, the reflector module 39 is configured as a particularly massive molded part, in which the scattering body 38 and at least one of the mirrors 11, 16 are together formed in such a way that no optically relevant border surface separates the scattering body 38 from the at least one mirror 11, 16. FIG. 17 shows, in a perspective plan view, and by way of example, a reflector module 39 with a scattering body 38 which is preferably embodied integrated, at the light outlet side. The scattering body 38 at the light outlet side of the reflector module 39 is embodied, for example, as a fluted structure formed on the molded part. The reflector module 39 is arranged in the illumination arrangement 06 in such a way that the parallel extending flutes of the fluted structure are preferably aligned with the movement direction 04 of the material 03. The mirrors 11, 16 and/or the lens 18 can be embodied to be integrated in the reflector module 39. Therefore, the reflector module 39 is preferably configured with a depression which is extending in the longitudinal direction of the illumination arrangement 06. The reflector module 39 is preferably constructed of several segments which are lined up with each other. Each segment constitutes the light beam path fed into the reflector module 39 by one of the light sources 07. The reflector module 39 is preferably mounted on the board 21, which is supporting the light sources 07, or on the support 27, by, for example, mounting elements 41 that are formed out of the reflector module 39. At least one reflector module 39 is preferably assigned to each one of the modules M61 to M65 which are arranged along the width B01 of the illuminated strip 01.

The scattering body 38 of the illumination arrangement 06, in a manner which is the same as the arrangement of the mirrors 11, 16 and/or of the lens 18, simultaneously acts in a shaping and homogenizing manner, with respect to the distribution of the light that is emitted by the light sources 07. The scattering body 38 contributes, in particular, to a shadow-free, diffused illumination of the illuminated strip 01, even on a surface 02 of the material 03 which may be provided with a delicate structure. Additionally, in spite of the distance A07 each of the light sources 07 has from the surface 02 of the material 03, the illuminated strip 01 is simultaneously formed as a very bright illuminated band because of the illumination arrangement 06. The arrangement of the mirrors 11, 16 and/or of the lens 18, as well as the provision of the scattering bodies 38 in particular, contributes to the light exiting the illumination arrangement 06 with a homogeneous light distribution. The result is that an inner structure of the illumination arrangement 06, such as, for example, the arrangement of its individual light sources 07, is not even represented on a reflecting surface 02 of the material 03, such as, for example, on a reflecting lacquer, a cold seal, a window thread, a patch, or the like. As a result, this arrangement of individual light sources 07 does not become visible even when viewed under the respective reflection angle.

FIG. 12 represents a side elevation view of the optical system, in accordance with the present invention. The view takes place from a plane extending perpendicularly with respect to the movement direction 04 of the material 03. The illumination arrangement 06 and the illuminated strip 01 which is illuminated by the illumination arrangement 06 on the surface 02 of the material 03 are arranged parallel, with respect to each other, at a distance A07. However, the extension of the illumination arrangement 06, i.e. its length B06, can, as seen in FIG. 12, be greater than the length L01 of the illuminated strip 01 or than the width B03 of the material 03. The illumination arrangement 06 is divided into several modules M61 to M65. In the example of FIG. 12, the illumination arrangement 06 is divided into five modules M61 to M65 which are arranged side-by-side in a line. The light sources 07, which is arranged in every module M61 to M65, respectively, emit light toward the illuminated strip 01. The light that is reflected by the now illuminated strip 01 is then detected by the detector 09 of the detection device 08, which detector 09 is arranged at a distance A09 from the surface 02 of the material 03, and within a spatial detection angle α which opens along the length L01 of the illuminated strip 01. The detection angle α is, in this depicted embodiment of such dimensions that it registers the light which is reflected at the illuminated strip 01 over the entire length of the illuminated strip 01. The detection angle α forms a cross-sectional area on the surface 02 of the material 03, so that the detection angle α registers at least a part of the cross-sectional area of the light beam which is emitted by the illumination arrangement 06 and which is extending over the width B01 of the illuminated strip 01. The cross-sectional area which is registered by the detection angle α preferably is at least as large as the area on the surface 02 of the material 03 that is defined by the length L01 and by the width 01 of the illuminated strip 01. The illumination arrangement 06 and the detection device 08 are preferably arranged spaced apart from each other in the movement direction 04 of the material 03 in such a way that the light which is emitted by the light sources 07 of the illumination arrangement 06 onto the surface 02 of the material 03 is reflected by the surface 02 of the material 03 toward the detector 09 of the detection device 08 in accordance with the rule "the angle of incidence is equal to the angle of reflection". However, the "angle of reflection" expected as a result of the "angle of incidence", or the reflection angle, can differ from the above mentioned ideal condition, which is based on a completely reflective area. This variation can be a result of the nature of the surface 02 of the material 03, and in particular can be a function of its structure, and in particular of its micro-structure.

The quality of an image that is taken by the detection device 08, by registering the light which is reflected at the illuminated strip 01, is substantially dependent on the fact that the light sources 07 of the illumination arrangement 06 can emit light at a constant intensity. Fluctuations in the intensity of the light which is emitted by the light sources 07 have the same result in the detection device 08, with regard to the signal provided to the image processing device 24, as would or do changes in the nature of the surface 02 of the illuminated material 03. The result is that the causes of a signal change cannot be detected in the image processing device 24. Under these circumstances, it is not possible to obtain dependable information regarding the nature of the surface 02 of the illuminated material 03 from an image evaluation which is performed in the image processing device 24.

Measures which maintain the intensity of the light emitted by the light sources 07 of the illumination arrangement 06 offer relief from the potential problem of light intensity variations. The light sources 07 used in the illumination arrangement 06 are preferably embodied as high-intensity light-emitting diodes 07 or as laser diodes 07, whose light intensity is a function of temperature. Steps that can be taken for stabilizing the temperature of the light sources 07, which are arranged on the support, in order to obtain a constant light intensity will be described subsequently. The advantage of the solution in accordance with the present invention lies in that the thermal load on the light sources 07 is removed directly at the place where it occurs. Because of this thermal load removal, it is possible to obtain short recovery times.

The light sources 07 are preferably arranged on a board 21, which can be equipped with additional electronic components and with strip conductors. The semi-conductor of the light-emitting diode 07 or of the laser diode 07 is preferably in direct contact with the board 21, which board 21 is configured as an MCPCB (metal core printed circuit board) or as a board 21 with a core of aluminum. Board 21 has, on its mounting side 32 which supports the light-emitting diodes 07 or the laser diodes 07, only a very thin cover on its heat-conducting base for forming the lowest possible heat transmission resistance.

Figure 13:
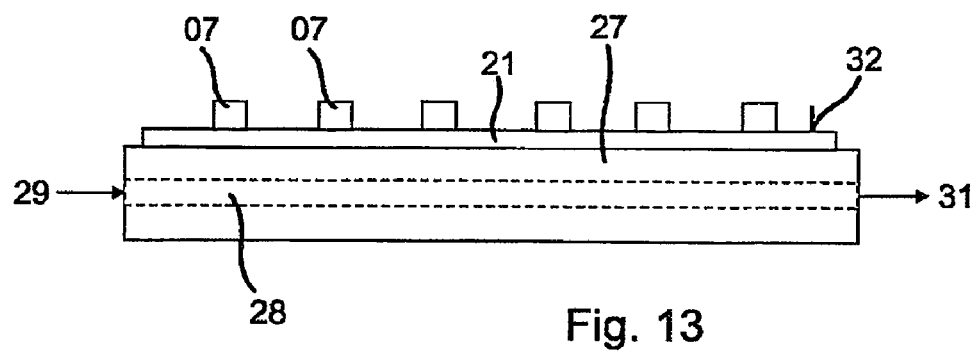
Figure 14:
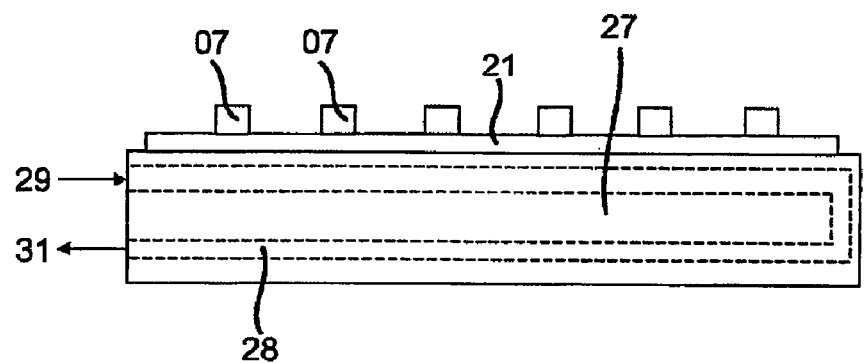

FIG. 13 shows a board 21 with several light sources 07 arranged in lines thereon. The board 21 itself is arranged on a support 27. Support 27 preferably has, in its interior, and preferably underneath the line-like or linear arrangement of the light sources 07, at least one conduit 28. A liquid or a gaseous coolant, such as, for example, water or air, flows through this conduit 28. An inflow opening 29 is connected with the coolant inflow, and a return flow opening 31 is connected with the return flow for use in feeding in and in removing the coolant. These openings are provided, preferably at the front or end face of the support. The coolant flows through the support 27, preferably in a straight line. FIG. 14 shows a support 27 through which the coolant flows in two opposite directions, because of which, a temperature profile is achieved in the support 27 which temperature profile is balanced along the line-shaped arrangement of the light sources 27. To accomplish this purpose, the conduit 28 can be reversed by 180□ at one end of the support 27 as seen in FIG. 14.

A regulating device, which is not specifically represented, can maintain the temperature of the coolant at the coolant inflow opening 29 and the flow-through quantity of the coolant passing through the conduit 28 constant. Alternatively, the regulating device can also maintain a constant difference between the temperature of the coolant at the inflow and the temperature of the coolant at the outflow. In this case, the absolute temperature of the coolant is of secondary importance. More importantly, a maximally permissible temperature for the light sources 07, which results from the heat transfer resistance of the involved materials, should not be exceeded. This is prevented by the regulating device, by monitoring the temperature of the light sources 07, or of the coolant and by reacting with corrective steps. If no coolant, whose temperature or flow-through quantity can be regulated, is available, cooling of the light sources 07 can also take place by the use of an external cooling device, which is not specifically represented, and which is not connected with the board 21.

Figure 15:
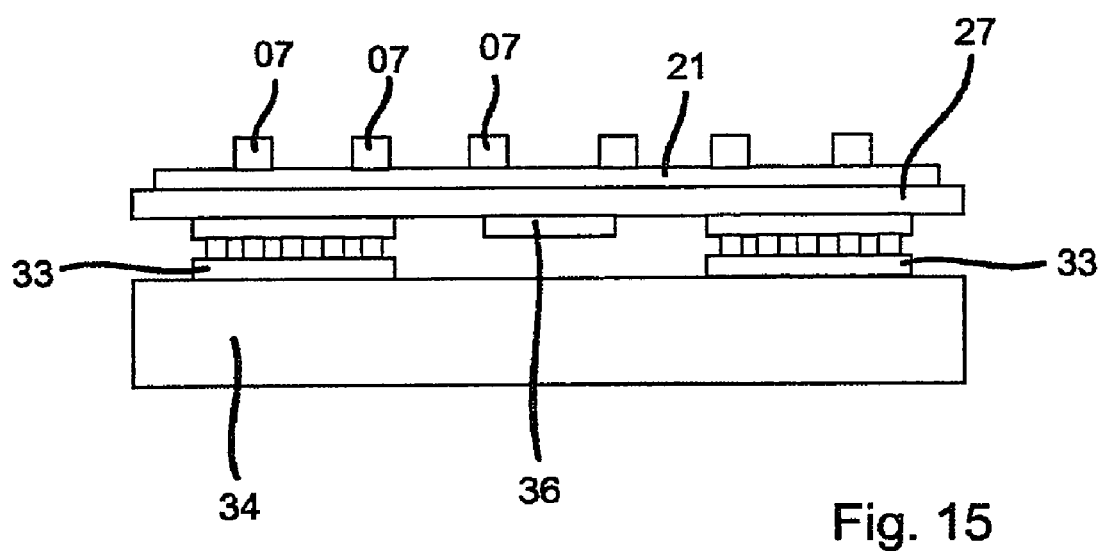

FIG. 15 shows an alternative to the use of a flowing coolant. The board 21, which is equipped with the light sources 07, is again arranged on a support 27. The support 27 itself is arranged on at least one Peltier element 33, and is preferably arranged on several such Peltier elements 33. The Peltier elements 33 are each connected with a cooling body 34 which is thermally separated from the support 27. A required temperature measurement, for use in regulating the at least one Peltier element 33, by an electronic regulating device, which is not specifically represented, is taken directly on the support 27 by a temperature sensor 36. In the case of a fluctuating ambient temperature, only the temperature of the cooling body 34 fluctuates. The temperature of the light sources 07 arranged on the board 21 does not fluctuate. The electronic regulating device can be integrated into the control device 23 which is connected with the illuminating arrangement 06.

Since the movement of the moving material 03 in a printing press, or in a machine which further processes a printed product, takes place at a speed of several meters per second, and, for example, at a speed of 3 m/s or more, and wherein in a sheet printing press, for example, 15,000 sheets 03 or more are imprinted per hour and are transported through the printing press, the optical system must be laid out in such a way that a usable image of the moving material 03 can be taken. Consideration must be given to the fact that, with a detection device 08 configured as a line-scanning camera 08, the detected amount of the light, which is reflected by the surface 02 of the moving material 03, changes as a function of the speed of the moving material 03. The brightness of the taken picture also changes as a function of the speed of the moving material 03. It is possible that the taken picture may be useless, in the case of greater speed changes, such as can customarily occur in the above-mentioned presses.

Instead of synchronizing the picture-taking of the detection device 08, such as, for example, the line-scanning camera 08, with the speed of the moving material 03 by the use of an encoder, it is proposed to synchronize a length of switched-on time t3 of a single light source 07 or of a group of light sources 07 of the illumination arrangement 06, which light source 07 or group of light sources 07 are preferably triggered by an electrical current source 22, and in particular by a constant electrical current source 22, which is controlled by the control device 23, with the triggering, or with the length of exposure time t1 of the line-scanning camera 08. The result is that the surface 02 of the moving material 03 is always illuminated with the same amount of light, independently of the speed of the moving material 03. From this a constant brightness of the picture taken by the detection device 08, such as, for example, by the line-scanning camera 08 results, over a wide range of the speed of the moving material 03. The control device 23 always sets the length of the switched-on time t3 of a single light source 07 or of a group of light sources 07 of the illumination device 06 lower than the length of exposure time t1 of the line-scanning camera 08.

As previously described, several groups of light sources 07 are preferably provided in the illumination arrangement 06. Each of the several groups of light sources 07 preferably has at least one electrical current source 22, and in particular has a constant electrical current source 22 assigned to it. The lengths of switched-on times t3 of the light sources 07 are controlled by the control device 23, which is connected with the illumination arrangement 06, for example in groups. These lengths t3 can also be controlled singly independently of each other by the respective electrical current sources 22. A profile of the amount of light can be set over the length of the light sources 07 of the illumination arrangement 06, which are preferably arranged in lines. Setting a profile of the amount of light, preferably along the length L01 of the illuminated strip 01, has the advantage that transmission losses can be compensated for by the use of an optical device, which is not specifically represented, of the detection device 08, for example the line-scanning camera 08.

It can moreover be provided that a light sensor 37, which is connected with the control device 23, as seen in FIG. 2, measures the amount of light that is radiated by the light sources 07 of the illumination arrangement 06. This can be done in order to match the length of the switched-on time t3 of the light sources 07, which are controlled by the control device 23, on the basis of the measuring signal of the light sensor 37, for example, to a degradation behavior of the light sources 07. By controlling the light sources 07, it is possible to compensate for a reduced output of the amount of light radiated because of aging of the light sources 07. Also, the control device 23 can match, and in particular can automatically match, the length of the switched-on time t3 of the light sources 07 with different optical properties of the material 03 to be illuminated, for example.

Figure 16:
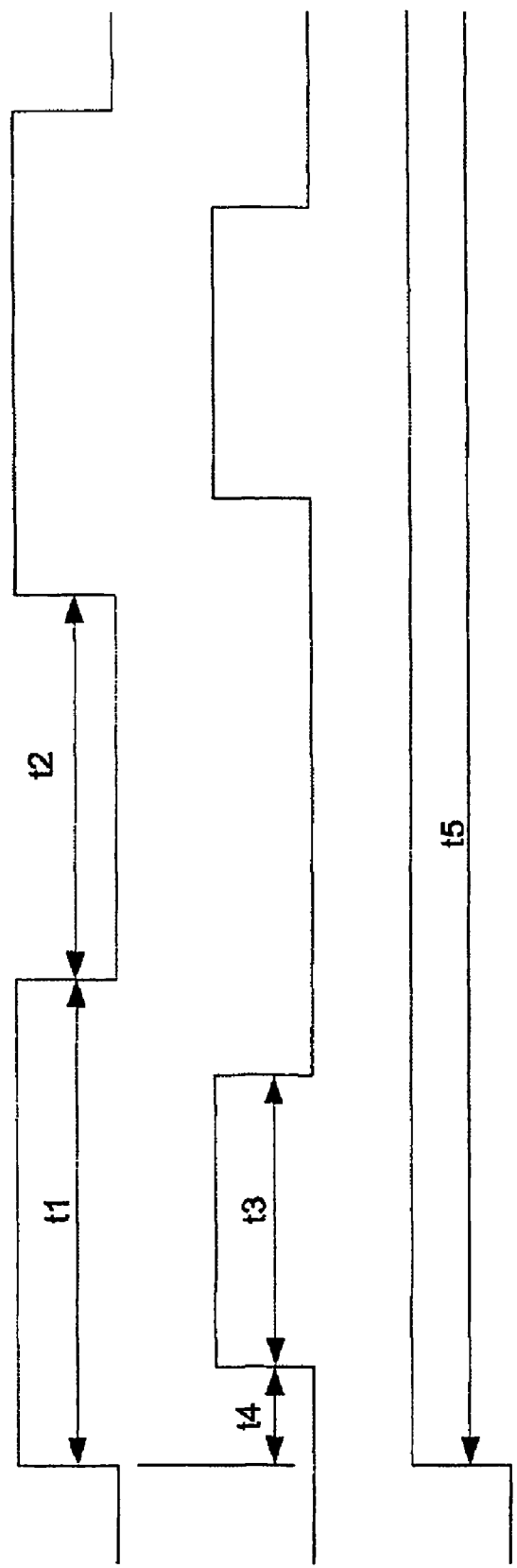

FIG. 16 shows the chronological behavior of the detection device 08, such as, for example, the line-scanning camera 08, and also shows the chronological behavior of the light sources 07 of the illumination arrangement 06. The line-scanning camera 08 is switched on at a defined point in time in accordance with the upper, first time progression of FIG. 16. The length of exposure time t1 of the line-scanning camera 08 starts at this point in time. Following the end of the exposure time t1, an off time t2, which is a function of the speed of the moving material 03, immediately follows between two adjoining image lines of the line-scanning camera 08 which follow each other in the movement direction 04 of the material 03. In accordance with the center, second time progression depicted in FIG. 16, at least one light source 07, which is triggered as a function of the control of the line-scanning camera 08, is turned on by the electrical current source 22, which is controlled by the control device 23 simultaneously with the length of exposure time t1 of the line-scanning camera 08. Following a delay time t4 for switching on the light source 07, or in other words, after a physically required time until the start of light emission, this light source 07 then remains switched on for a length of switched-on time t3. The length of switched-on time t3, and preferably also a sum of the times consisting of a delay time t4 and of the length of switched-on time t3, is of shorter length than is the length of exposure time t1 of the line-scanning camera 08. The chronological behavior of the line-scanning camera 08 and of the light sources 07 is periodically repeated in accordance with the above-described correlation. The chronological behavior of the switched-on time t5 for a constant light source is represented in the lower, third time progression in FIG. 16 only as a comparison with the chronological behavior of the triggered switched-on time t3 of the light source 05.

While a preferred embodiment of an optical system for forming an illuminated pattern, in accordance with the present invention, has been set forth fully and completely herein above, it will be apparent to one of skill in the art that various changes, for example in the type of images being processed, in the apparatus used for moving the material in a movement direction and the like could be made without departing from the true spirit and scope of the present invention which is accordingly to be limited only by the appended claims.

What is claimed is:

1. An optical system adapted to generate an illuminated pattern on a surface of a material comprising:
   a material support unable support said material for movement of said material relative to said illuminated pattern at a variable transport speed in a transport direction;
   an illumination arrangement including a plurality of light sources, said illumination arrangement being usable to generate said illuminated pattern on said surface of said material moving at said variable transport speed as an illuminated strip having a strip width in said transport direction;

a detection device usable to detect light emitted by said light sources;

a control device usable to selectively operate one, and a group of said plurality of light sources, in a pulsed manner;

a light source chronological behavior of at least one light source of said plurality of light sources, said light source chronological behavior including a light source switched-on time length, a light source switching-on delay time length immediately preceding said light source switched-on time, and a light source switched-off time length subsequent to said light source switched-on time, said light source switched-on time length being a function of said variable transport speed and of optical properties of said material;

a detection device chronological behavior of said detection device, said detection device chronological behavior including a detection device exposure time length and a detection device off time length, said detection device off time length immediately following said detection device exposure time, said detection device off time length being set as a function of said variable transport speed of said material, said light source switched-on time length and said immediately preceding light source switching-on delay time length being synchronized with, and being less than said detection device exposure time length;

a first time sum set by said control device and including said light source switching-on delay time length and said light source switched-on time length; and a second time set by said control device and including said detection device exposure time length, said second time being greater than said first time sum, said light source switched-on time length and said light source switching-on delay time length being completely within said detection device exposure time length which is greater than said light source switching-on delay time length and said light source switched-on time length, said surface of said material being illuminated with a constant amount of light independently of said variable transport speed of said material.

2. The optical system of claim 1 wherein said control device is usable to switch said light source on simultaneously with a start of said detection device exposure time.

3. The optical system of claim 1 further including an electrical current supply assigned to said illumination arrangement and being controlled by said control device.

4. The optical system of claim 1 wherein said detection device is a line-scanning camera.

5. The optical system of claim 1 further including several groups of said light sources in said illumination arrangement.

6. The optical system of claim 1 wherein said plurality of light sources are arranged as lines in said illumination arrangement and further wherein a profile of an amount of light is produced by control of said light sources over a length of their arrangement as said lines.

7. The optical system of claim 1 further including a light sensor connected with said control device and usable to measure an amount of light emitted by said light sources.

8. The optical system of claim 1 wherein said detection device includes a plurality of detectors arranged next to each other in the shape of lines.

9. The optical system of claim 1 wherein at least one light source of said illumination arrangement emits a constant amount of light during said light source switched-on time length.

10. The optical system of claim 5 further including at least one electrical current source controlled by said control device and assigned to each of said several groups of said light sources.

11. The optical system of claim 10 wherein each said electrical current source is a constant electrical current source.

12. The optical system of claim 6 wherein said profile is set along a length of an illuminated strip.

13. The optical system of claim 7 wherein said control device matches said switched-on time length of said light sources to a degradation behavior of said light sources by use of said light sensor.

14. The optical system of claim 7 wherein said control device compensates for a reduction in an amount of light emitted by said light sources, as a result of their aging, by use of said measured signal from said light sensor.

15. The optical system of claim 8 wherein said detectors arranged next to each other in the shape of lines are arranged parallel to one of a length of said illuminated strip formed as said illuminated pattern and a width of said material.

16. The optical system of claim 8 wherein a spacing between said lines of detection and said direction of movement of said material, is orthogonal.

* * * * *

UNITED STATES PATENT AND TRADEMARK OFFICE
CERTIFICATE OF CORRECTION

PATENT NO. : 7,635,830 B2 Page 1 of 1
APPLICATION NO. : 10/593728
DATED : December 22, 2009
INVENTOR(S) : Carsten Diederichs It is certified that error appears in the above-identified patent and that said Letters Patent is hereby corrected as shown below:

Column 14, in claim 1, line 59, after "material support", change "unable" to -- usable to --

Signed and Sealed this

Thirteenth Day of April, 2010

David J. Kappos
*Director of the United States Patent and Trademark Office*